United States Patent [19]
Suh et al.

[11] Patent Number: 5,916,917
[45] Date of Patent: Jun. 29, 1999

[54] DUST MITE CONTROL COMPOSITIONS CONTAINING BENZYL BENZOATE AND ALCOHOL

[75] Inventors: Janette Suh, Mahwah; Laura Vaccaro, Montclair; Robert Bogart, River Vale; Dennis Smialowicz, Waldwick, all of N.J.

[73] Assignee: Reckitt & Colman Inc., Wayne, N.J.

[21] Appl. No.: 09/013,594

[22] Filed: Jan. 26, 1998

[51] Int. Cl.$^6$ ................................................ A01N 37/10
[52] U.S. Cl. ............................................................. 514/544
[58] Field of Search .......................... 424/288; 514/255, 514/425, 544, 532

[56] References Cited

U.S. PATENT DOCUMENTS

| | | | |
|---|---|---|---|
| 4,224,338 | 9/1980 | Sbragia et al. | 424/288 |
| 4,666,940 | 5/1987 | Bischoff et al. | 514/544 |
| 4,800,196 | 1/1989 | Nomura et al. | 514/159 |
| 4,806,526 | 2/1989 | Green | 514/23 |
| 5,045,560 | 9/1991 | Fischer et al. | 514/425 |
| 5,057,527 | 10/1991 | Alig et al. | 514/345 |
| 5,180,586 | 1/1993 | Sato et al. | 424/405 |
| 5,271,947 | 12/1993 | Miller et al. | 424/680 |
| 5,719,114 | 2/1998 | Zocchi et al. | 510/383 |

FOREIGN PATENT DOCUMENTS

| | | | |
|---|---|---|---|
| B-69067/87 | 8/1987 | Australia | A01N 53/00 |
| 2111526 | 6/1994 | Canada . | |
| 0612469 | 8/1994 | European Pat. Off. | A01N 25/00 |
| 60-42314 | 3/1985 | Japan . | |
| 60-142906 | 7/1985 | Japan . | |
| 61-91103 | 5/1986 | Japan . | |
| 1-100101 | 4/1989 | Japan | A01N 33/12 |
| 3-31206 | 2/1991 | Japan . | |
| 5-262604 | 10/1993 | Japan . | |
| 1368657 | 10/1974 | United Kingdom | A01N 9/24 |
| 2042893 | 1/1980 | United Kingdom . | |
| WO 89/12673 | 12/1989 | WIPO | C11D 3/48 |
| WO89/12673 | 12/1989 | WIPO | C11D 3/48 |

OTHER PUBLICATIONS

Schober et al. "Control of House–Dust Mites (Pyroglyphidae) With Home Disinfectants", Experimental & Applied Acaralogy, 3 (1987) 179–189.

Le Mao et al., "Changes in Mite Allergen Levels in Homes using an Acaricide Combined with Cleaning Agents: A 3–Year Follow–Up Study", The Journal of Indoor Air International, 1992, 1:212–218.

Manjra, A., et al. "The effects of a single treatment of an acaricide . . . ", S. Afr. Med. J. 84:278 (1994) Abstract.

Hart, B., et al. "In–vitro evaluation of acaricidal and fungicidal activity . . . ", Clin. Exp. Allergy 22:923 (1992) Abstract.

*Primary Examiner*—Jose'G. Dees
*Assistant Examiner*—Alton Pryor
*Attorney, Agent, or Firm*—Fish & Richardson P.C.

[57] ABSTRACT

An alcohol based disinfecting composition which contains from 0.1% to 10% of benzyl benzoate is effective in killing dust mites. The compositions can comprise additional disinfectants and are most conveniently applied in aerosol form with a suitable propellant. Allergens contained in the faecal matter excreted by dust mites can be controlled by removing dead mites and associated faecal matter using a vacuuming apparatus under conditions which do not cause the removed material to vent into the ambient atmosphere.

18 Claims, No Drawings

DUST MITE CONTROL COMPOSITIONS CONTAINING BENZYL BENZOATE AND ALCOHOL

BACKGROUND OF THE INVENTION

This invention relates to alcohol-based disinfectant compositions containing a miticidally effective ingredient. More particularly, the invention relates to spray disinfectants suitable for indoor use which, in addition to having the usual antimicrobial properties, are also effective to kill dust mites and to be useful in a method for controlling dust mite allergens. The invention also relates to a method for killing dust mites and for controlling the allergens produced by them.

Common house dust is an important cause of asthma, rhinitis, atopic dermatitis eczema in allergic individuals. The mite *Dermatophygoides pteronyssinus* has been identified as a major source of house dust allergen. This mite and the related mites *D. farinae, D. microceras* and *Euroglyphus maynei* are the predominant house dust mites in temperate climates in North America, Australia and other areas.

Dust mites are not insects, but are eight-legged arachnids, relatives to ticks and spiders. They live in close association with humans (or other mammals), their main food source being the shed scales from skin. Adult mites are approximately 300 microns (3/10 mm) in size, having developed over approximately 25 days through egg, larval and nymph stages. Adults live for 2 to 3-½ months, during which time each female can produce about 20–40 eggs. Dust mites are photophobic, living deep in pillows, mattresses, carpets, upholstered furniture and other soft materials.

In addition to a food source, the other essential requirement for dust mite growth is adequate humidity. Dust mites are 75% water by weight. They do not drink water, but must absorb water vapor from the air in order to survive. Specialized glands above their pairs of legs produce secretions high in sodium and potassium chloride, which act to absorb water vapor from surrounding air. This can only be accomplished if the surrounding humidity is sufficiently high. Relative humidities of about 65–80% at temperatures ranging from about 20° to 35° C. are optimal for dust mite growth. Dust mites will die at humidities of 50% or less. In geographical areas where humidity is high, dust mites are present in nearly all homes and may be as plentiful as 18,000 mites per gram of dust. Literally millions of mites can inhibit a single bed or rug.

A major dust mite allergen is present in mite faecal particles. Each mite produces about 20 faecal particles per day, and more than 100,000 of them may be present in a gram of dust. These particles vary from about 10 to 40 microns in size, comparable to the size of pollen grains, and become airborne during domestic activity such as making beds and vacuuming carpets.

Group I allergens (dermatophagoides farinae I - Der f I and dermatophagoides pteronyssinus I - Der p I) are heat labile, 24,000 molecular weight glycoproteins (hydrolytic enzymes). These allergens appear to be structural homologues and have very similar N-terminal amino acid sequences. These group I allergens are regarded as the most important and are excreted in their highest concentrations by the mite's gastrointestinal tract in the form of mite's faecal particles, suggesting that they are associated with digestion. They elute rapidly (within 2 minutes) from isolated faecal particles, but very slow from mite bodies.

Group II allergens (Der p II and Der f II) are 15,000 molecular weight proteins with almost identical N-terminal amino acid sequences that are also secreted by the mite's gastrointestinal tract in the form of faecal allergens, although not in as high a concentration as the group I allergens. This suggests that they probably derived from a a source other than the gut. Their actual function has not been determined.

Most mite-allergic individuals produce antibodies to both the group I and group II allergens.

| Allergen | Mol. Weight | pH |
|---|---|---|
| Group I | | |
| Der p I | 24,000 | 4.6–7.4 |
| Der f I | 24,000 | 4.6–7.4 |
| Group II | | |
| Der p II | 15,000 | 5.0–6.4 |
| Der f II | 15,000 | 7.8–8.3 |

Acute exposure to mite allergens has been shown to induce wheezing, rhinitis, eustachian tube obstruction or eczema in sensitized patients. Chronic exposure can cause bronchial hyper-reactivity and chronic asthma. There is a correlation between the level of exposure to house dust mite allergen in early childhood and the likelihood of the subsequent development of asthma. Conversely, asthmatics sensitive to dust mites improve in environments without mites, such as at high altitudes or in hospital rooms. Attempts have therefore been made to decrease patients' exposure to dust mites in the home.

Studies of dust avoidance measures in homes have shown that the use of impermeable mattress and pillow encasings and the removal of bedroom carpeting are associated with a decrease in mite counts. These measures have also been shown to be of clinical value, with a decrease in symptoms and medication requirements occurring in children and adults with dust-sensitive asthma when pillows and mattresses are encased and carpets are removed.

Although carpets and upholstered furniture are major sites of dust mite growth, many allergic individuals are unable or unwilling to remove these from their home. Ordinary vacuuming does not remove dust mites or significantly decrease dust mite allergen levels, and in fact, vacuuming of carpets with the usual household appliances actually increases the amount of airborne dust. However, the use of special filters such as HEPA (High Efficiency Particulate Air) filters or two-ply vacuum bags, and/or the employment of central vacuuming systems (where the dust is collected in a receptacle remote from the room being cleaned) have been helpful. Nevertheless, vacuuming seldom removes all of the live mites, mainly because the mites have little suction cups on the tops of their legs which cause them to cling to textile fibres.

Various chemical agents have been used against mites, including: compounds known under the common names as resuethrin, phenothrin, permethrin, allethrins, tetramethrin, furamethrin, cypermethrin, decamethrin, phenvalerate, phenpropathrin, terallethrin, empenthrin and pyrethrin; pyrethroid compounds such as 1-ethynyl-2-methyl-2-pentenyl-2,2-dimethyl-3-3-(2,2-dichlorovinyl)-cyclopropane-1-carboxylate, 1-ethynyl-2-methyl-2-pentenyl-2,2,3,3-tetramethylcyclopropane-1-carboxylate, α-cyano-3-phenoxybenzyl-2,2-dimethyl-3-(2,2,3-tribromethyl)-cyclopropane-1-carboxylate; organic phosphorus compounds such as sumithion, fenthion, tetrachlorvinphos, diazinon and DDVP; and carbamate compounds such as those sold under the trademarks Baygon and Sevin. However, these conventional miticides are expensive and are often either toxic to human beings or have the potential to cause allergic or other adverse reactions. Therefore, the use of such compounds in a household environment cannot be the solution to controlling the population of dust mites.

A number of less toxic miticidal agents have been proposed for use in controlling dust mites. As noted in U.S. Pat. No. 4,800,196, these include phenyl salicylate, diphenylamine, methyl β-naphthyl ketone, coumarin, phenethyl benzoate, benzyl salicylate, phenyl benzoate, N-fluorodichloromethylthio-cyclohexene-dicarboxyimide, p-nitrobenzoic acid methyl ester, p-chlorometaxylenol, α-bromocinnamic aldehyde, 2,5-dichloro-4-bromophenol, N,N-dimethyl-N'-tryl-N'-(fluorodichloromethylthio)-sulfamide, 2-phenylphenol, sodium 2-phenylphenolate, 5-chloro-2-methyl-4-isothiazoline-3-one, 2-methyl-4-isothiazoline-3-one and benzimidazolylmethyl-carbamate. These can be used in the form of solutions, wetable powders, granules, sprays, etc.

While many of these compounds have some degree of effectiveness against dust mites, their use is not without attendant shortcomings. For example, many of them are rather expensive to produce and/or may be difficult to form into compositions for ordinary domestic use. Elimination of dust in a household environment is a task which is intensely disliked to the point where the average householder is no longer embarrassed by a moderate layer of dust or the presence of "dust bunnies" under beds or behind furniture. Furthermore, as noted above, dust removal and/or vacuuming often stirs up the dust mites and their attendant allergens and, temporarily at least, causes more distress to allergic persons.

Thus, it would be desirable to have a simple and effective method of controlling the allergens provided by dust mites, regardless of whether the householder is diligent in removing dust. It would also be desirable to have a method for controlling said allergens which does not involve stirring up said allergens.

U.S. Pat. No. 5,271,947 features the use of finely divided sodium chloride powder as a method for killing mites and controlling their allergen-bearing faeces. The powder has the consistency of talcum powder and is used, for example, by applying the powder with a broom or brush to carpets and other textile materials. However, one of the disadvantages in using sodium chloride powder is its hygroscopicity; if the amount used is not carefully controlled, the salt will absorb moisture from the air, particularly in humid climates.

One of the more effective agents for killing dust mites is benzyl benzoate, a compound which is readily available and inexpensive. Powder formulations containing benzyl benzoate are commercially available for application to carpets. British Patent No. 1,368,657 teaches the use of a composition for treating bedding and similar materials which comprises benzyl benzoate and polyethylene glycol or an ether or ester thereof. British Patent No. 2,042,893 teaches the use of a composition comprising benzyl benzoate and a fatty acid ester for application to bedding and also for treating the skin. A similar composition for general miticidal use in households is taught in published Japanese Patent Application No. 61-91103.

More generally, Bischoff U.S. Pat. No. 4,666,940 teaches the use of various miticidal agents, including particularly benzyl benzoate, as a component in cleansing compositions. European Patent Application No. 0,612,469 discloses laundry detergents comprising benzyl benzoate, which compositions are taught to be effective in killing the dust mites present on the articles to be laundered.

In an article by G. Schober et al., "Control of House-Dust Mites (Pyroglyphidae) with Home Disinfectants", *Experimental & Applied Acarology* 3:179-89 (1987), the authors provide data showing that the addition of benzyl benzoate to certain commercially available carpet cleaning formulations results in a composition with better acaricidal properties than other known acaricides.

U.S. Pat. No. 5,180,586 discloses that certain compounds, previously known for use as perfuming agents in foods and cosmetics, have been found to be effective in killing dust mites.

According to the published literature, benzyl benzoate and other miticidal compounds disclosed in the art can, under proper conditions of use, be effective in killing dust mites and thus eventually reducing the level of allergens. Laundering and dry cleaning of textiles and fabrics, while effective under certain conditions, require a considerable amount of effort and, unless all of the infested areas are treated within a short period of time, the dust mite population will not be permanently reduced.

Likewise, an aerosol spray formulation with benzyl benzoate or another miticidally active compound would, with proper formulation and on the proper conditions of use, be effective in killing dust mites and controlling their allergen-bearing faecal matter. However, it is perceived that there is a problem with consumer acceptance of a product of this nature.

In view of the fact that dust mites are invisible to the naked eye, it is logical, from a commercial point of view, to kill dust mites simultaneously with killing other invisible organisms such as bacteria. Aerosol disinfectant compositions have attained wide consumer acceptance and the addition of an ingredient which would kill dust mites and facilitate the control of dust mite allergens would have an extremely beneficial purpose without the necessity of having to persuade potential consumers to purchase an additional household care product. Furthermore, an aerosol spray formulation would not have the attendant temporary adverse effect of stirring up the dust mites and their faecal particles and thereby causing allergic reaction.

Since dust mites dwell in textile materials such as mattresses, rugs, pillows, upholstered furniture and other interior furnishings, it is a principal object of this invention to provide a method for controlling dust mite allergens by killing mites on such textile surfaces and simultaneously sanitizing said surfaces and the surrounding area.

It is a further object of this invention to provide a method for controlling dust mite allergens which includes, in addition to simultaneously killing the mites and sanitizing the textile surfaces infected with said mites, the immediate and effective removal of said allergen.

And another object of this invention is to fulfill the aforementioned object by employing a composition comprising a known disinfecting agent and benzyl benzoate as the miticide.

And it is also an object of this invention to provide compositions intended for use in the above-described methods.

SUMMARY OF THE INVENTION

This invention provides alcohol-based disinfecting compositions which additionally contain from about 0.1% to about 10% of benzyl benzoate as an acaricidal ingredient.

Said compositions, in addition to their usual disinfecting properties, also kill dust mites. The compositions can also comprise one or more additional disinfectants such as a quaternary ammonium compound, a phenol-based antimicrobial agent, or a botanical oil with disinfectant properties. The compositions are most conveniently supplied in aerosol form with a suitable propellant.

The allergens contained in the faecal matter excreted by dust mites can be controlled by applying, more particularly, by spraying, the compositions of this invention onto the surface of textile fabrics intended with said mites. The mites are thus killed and the production of additional allergens thereby halted. However, for more immediate control, dead mites and faecal matter should be removed preferably by employing a vacuuming apparatus under conditions which do not cause the removed material to vent into the ambient atmosphere.

DETAILED DESCRIPTION OF THE INVENTION

The compositions of this invention comprise, as essential ingredients, benzyl benzoate and an alcohol having from 1 to 4 carbon atoms, preferably ethanol. The methods of this invention comprise the steps of (1) providing a sprayable composition comprising benzyl benzoate and a $C_1$ to $C_4$ alcohol, preferably ethanol, (2) spraying said composition onto a textile fabric surface such as rugs, pillows, upholstered surfaces, etc., (3) allowing a suitable period of time for the surface to dry, and (4) vacuuming up the dead mites and associated faecal matter under conditions where the material vacuumed up cannot vent into the ambient atmosphere. Steps (1) and (2) alone will prevent the deposition of additional allergen-bearing faecal matter but, for more effective and immediate control of the allergens, steps (3) and (4) are required.

The alcohol functions as both solvent and disinfectant. The subject compositions can contain other disinfecting components as well as additional ingredients. Preferred additional ingredients include surfactants, preservatives, pH adjusting agents, corrosion inhibitors, etc.

The amount of benzyl benzoate in the compositions is from about 0.1 to 10% by weight (excluding the propellant required in aerosol compositions). Preferably, benzyl benzoate is present in an amount ranging from 2.0% to 8.0%, more preferably from 3.0 to 7.0%.

As contemplated by this invention, the principal disinfecting ingredient is a low molecular weight alcohol, typically an alcohol having from 1 to 4,carbon atoms such as methanol, ethanol or isopropanol, with ethanol being, preferred. The disinfecting-properties of such alcohols are well known. They form the basis of many commercial disinfecting compositions and such compositions have attained great consumer acceptance. In addition to its disinfecting properties, the alcohol also functions as a solvent for some of the ingredients optionally present in the compositions of this invention and provides for rapid drying time in a household environment. Most importantly, however, it has been discovered that, particularly when ethanol is employed, the alcohol enhances the effectiveness of the compositions. Without wishing to be bound by any particular theory, it is believed that ethanol stuns the mites and aids in the penetration of the composition into the mites' bodies.

The amount of alcohol present in the composition ranges from about 10% to 95%, preferably from 50% to 85%, based on the weight of the composition (excluding the propellant required in aerosol compositions).

The compositions of this invention also preferably contain one or more additional antimicrobial agents in order to increase the antimicrobial effectiveness of the composition up to a level defined by the United States Environmental Protection Agency as "hospital strength disinfection". The term, "hospital strength" is not intended to indicate that the subject compositions are restricted to use in hospitals and other health care facilities; rather such disinfectant compositions are commonly sold for domestic use, and the term simply indicates a somewhat higher level of disinfective activity.

Although any known disinfecting agent can be used as an optional additional component, preferably the disinfectant agent will comprise one or more quaternary ammonium compounds commonly used as disinfectants, or one or more of the well known phenolic compounds such as ortho-phenylphenol, or an antimicrobial botanical oil. The antimicrobial ingredient is present in the composition in amounts ranging from about 0.01 weight percent to about 1 weight percent, preferably from 0.05 to 0.5 weight percent, and more preferably about 0.1%, based on total weight of the composition (excluding the propellant present in aerosol compositions).

If the antimicrobial component is a quaternary ammonium salt, any of the broad classes of suitable quaternary ammonium compounds may be used. More than one quaternary ammonium compound is employed to assist in providing a broader spectrum antimicrobial efficacy. Useful quaternary ammonium compounds include, for example, those quaternary ammonium compounds represented by the formula:

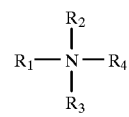

wherein $R_1$, $R_2$, $R_3$, and $R_4$ may be described in three general groups.

In a first group of preferred quaternary ammonium compounds, $R_1$ and $R_2$ are $C_1$–$C_7$ alkyl groups (preferably methyl groups); $R_3$ is a benzyl group or a benzyl group substituted with an alkyl group having about 1 to 18 carbon atoms or an alkyl group having about 8 to 20, and preferably 8 to 18, carbon atoms; $R_4$ is a benzyl group or a benzyl group substituted with an alkyl group having about 1 to 18 carbon atoms, and $R_4$ is a benzyl group or a benzyl group substituted with an alkyl group having about 1 to 18 carbon atoms or an alkyl group having about 8 to 20, and preferably 8 to 18, carbon atoms.

In a second group of preferred quaternary compounds, $R_1$, $R_2$ and $R_3$ are $C_1$ to $C_7$ alkyl (preferably methyl groups); and $R_4$ is an alkyl, an alkyl-substituted benzyl, or a phenyl-substituted alkyl group having a total of from about 8 to 20, and preferably 8 to 18, carbon atoms.

In a third group of preferred quaternary ammonium compounds, $R_1$ is an alkyl, an alkyl substituted benzyl, or a phenyl substituted alkyl group having a total of from about 10 to 20, and preferably from 12 to 16, carbon atoms; $R_2$ is a $C_1$–$C_7$ alkyl (preferably a methyl group); $R_3$ is [—$CH_2CH_2O$—]$_x$H; and $R_4$ [—$CH_2CH_2O$—]$_y$H, with the sum of x+y varying between about 2 and 50 (preferably 2 and 5). For all these groups, X may be a halide (preferably chloride or bromide) or may be a suitable organic anion such as benzoate or saccharinate.

Quaternary ammonium compounds are well known and available commercially from a number of suppliers. For example, dialkyl dimethyl ammonium chloride is available in approximately 50% active ingredient solution as BARDAC™-2050 quaternary ammonium compound from Lonza, Inc. (Fairlawn, N.J.) and BIO-DAC™-50-20 quaternary ammonium compounds is available from Bio-Labs (Decatur, Ga.), both of which are mixtures of approximately 25% octadecyl dimethyl ammonium chloride, about 10% dioctyl dimethyl ammonium chloride, about 15% didecyl dimethyl ammonium chloride in a solvent solution containing about 10–20% ethyl alcohol and 30–40% water. Also, for example, alkyl dimethyl benzyl ammonium chloride is available in an approximately 80% active ingredient solution as BTC™-8358 from Stepan Co. (Northfield, Ill.); BIO-QUAT™-80-28RX from Bio Lab, and BARQUAT™-MB80-10 is available from Lonza, both of these have an alkyl distribution of approximately $C_{14}$ (50%), $C_{12}$ (40%) and $C_{16}$ (10%) and diluents of ethyl alcohol (10%) and water (10%). In addition, a dialkyl dimethylbenzyl ammonium saccharinate in 33% alcohol solution is available from Stepan Company as ONYXIDE 3300.

If the antimicrobial ingredient is a phenolic derivative, any suitable phenol compound may be used. These include phenol itself, halogenated phenols, phenylphenols, xylenols, nitrophenols, cresols, thymol, nitrophenols, aminophenols, and many others well known in the art.

The antimicrobial botanical oils contemplated for use in the subject compositions are those essential oils which can form a solution or dispersion when combined with a water carrier and, when necessary, the addition of a solubilizing or dispersing agent. Such essential oils include, but are not limited to, those obtained from thyme, lemon grass, lemons, oranges, anise, clove, roses, lavender, citronella, eucalyptus, peppermint, camphor, sandlewood, cedar, etc., and combinations thereof.

The compositions of this invention may also include one or more surfactants in concentration ranging from 0.035 to about 10 weight percent, preferably from 0.04 to 2 weight percent based on the total weight of the composition (excluding the propellant required in aerosol formulations). The surfactants can be cationic, anionic, or nonionic. However, when the compositions contain a quaternary ammonium compound as an additional disinfecting agent, the surfactants present should be limited to nonionic surfactants.

Examples of suitable nonionic surfactants are as follows: Ethoxylated fatty alcohols containing from 11 to 15 carbon atoms in the alcohol and from 3 to 40 moles of ethylene oxide (Tergitol Nonionics; Union Carbide Corporation), such as isomeric linear secondary alcohols with 11 to 15 carbon atoms and 9 moles of ethylene oxide (Tergitol 15-S-9), and linear primary alcohols with 12 to 15 carbon atoms and 9 moles of ethylene oxide (Tergitol 25-L-9); the block copolymers of polyoxyethylenepolyoxypropylene ("Tetronic® Series Nonionic Surfactants", BASF Wyandotte Corporation) and ethylene glycol-reacted polyoxyethylene-poly-oxy-propylene copolymers of the formula $[HO(CH_2C-H_2O)_x(CHCH_3-CH_2O)_y(CH_2CH_2O)_z]_2H$, such as, for example, where x, y and z respectively are 13, 30 and 13 (Pluronic L-64; BASF Wyandotte Corporation); alkyl phenol ethoxylates such as nonylphenoxypolyethoxyephenol ethoxylates such as nonylphenoxypolyethoxyethanol with 9 to 10 moles of ethylene oxide (Triton N-101; Rohm & Haas Co.); alkanolamides for example, fatty acid alkanolamides having one or two hydroxyethyl or hydroxypropyl groups such as coconut and tallow fatty acid ethanolamide and diethanolamide; and oleic acid diethanolamide; silicone glycol copolymers such as those sold as Dow Corning 190, 193 or 1315.

Particularly useful nonionic surfactants are amine oxides, which include alkyldi(lower alkyl)amine oxides in which the alkyl group has about 10–20, and preferably 12–16 carbon atoms, and can be straight or branched chain, saturated or unsaturated. The lower alkyl groups include between 1 and 7 carbon atoms. Examples include lauryldimethylamine oxide, myristyldimethylamine oxide, and those in which the alkyl group is a mixture of different amine oxides, such as dimethyl cocoamine oxide, dimethyl (hydrogenated tallow) amine oxide, and myristyl/palmityl dimethylamine oxide.

A further class of useful amine oxides include alkyl di(hydroxy lower alkyl)amine oxides in which the alkyl group has about 10–20, and preferably 12–16, carbon atoms, and can be straight or branched chain, saturated or unsaturated. Examples are bis(2-hydroxyethyl) cocoamine oxide, bis(2-hydroxyethyl) tallowamine oxide, and bis(2-hydroxyethyl) stearylamine oxide.

Further useful amine oxides include those which may be characterized as alkylamidopropyldi(lower alkyl)amines in which the alkyl group has about 10–20, and preferably 12–16, carbon atoms, and can be straight or branched chain, saturated or tallowamidopropyl dimethyl amine oxide.

Additional useful amine oxides include those which may be referred to as alkylmorpholine oxides in which the alkyl group has about 10–20, and preferably 12–16, carbon atoms, and can be straight or branched chain, saturated or unsaturated.

Further examples of such useful amine oxides include ionic surfactant compositions based on amine oxides include those which are commercially available. Particularly useful are those under the trademark AMMONYX, i.e., AMMONYX CDO (cocoamide propyl dimethyl amine oxide); AMMONYX Co (cetyl dimethyl amine oxide); AMMONYX DMCD-40 (lauryl dimethyl amine oxide); AMMONYX LO (lauryl dimethyl amine oxide); AMMONYX MCO (myristyl cetyl dimethyl amine oxide); AMMONYX MO (myristyl dimethyl amine oxide).

It is believed that benzyl benzoate acts in a two-fold way in killing mites. First, the substance is toxic to the mite larvae. Secondly, it is believed that, when an aerosol spray comprising benzyl benzoate is sprayed onto adult mites, the product benzyl benzoate adheres to the mite and prevents respiration. The alcohol in the compositions of this invention hastens the drying process and therefore provides an enhanced level of toxicity as compared to some other solvents such as water and glycols.

The compositions of this invention should have a pH in the range of 8 to 11. In order to attain a suitable pH, it is usually necessary to add alkalizing agents which include well-known substances such as sodium hydroxide, potassium hydroxide, ammonium hydroxide, mono-, di- and tri-ethanol amines, and other agents well known in the art.

The compositions of the invention may also include one or more optional constituents including, but not limited to: pH buffering agents, preservatives, fragrances, fragrance carriers and adjuvants which increase their miscibility in the aqueous compositions, colorants, hydrotropes, antifoaming agents, anti-oxidants, corrosion inhibitors particularly when formulated for use in a pressurized aerosol container, as well as other known to the art but not particularly elucidated herein.

In a preferred form, the compositions of this invention are supplied in self-contained valve controlled aerosol units which provide a fine spray or foam upon activation of the valve. The aerosol container unit consists of a pressure-tight aerosol container having a valve control opening and containing the aqueous composition of this invention and from about 2 to about 10% of a propellant. Propellants are selected from the well known compatible propellants such as carbon dioxide isobutane, n-butane, n-propane and mixtures thereof. The propellant used should not adversely react with any components of the composition.

In the methods according to this invention, the subject compositions are applied to textile surfaces such as rugs, carpets, bedding, pillows, etc. known to be infested with dust mites. The preferred mode of application is by means of aerosol spraying device. Spraying should be carefully done, ensuring that, for example, all sides of pillows are sprayed, that the spray reaches to corners and crevices, etc. The spraying step alone will eventually reduce the amount of allergens by reducing the deposition of additional allergen-containing faecal matter. However, for more immediate and effective control, the dead mites and previously deposited faecal matter should be removed. Therefore, after a period of time sufficient to permit the spray to dry and ensure that the mites have been killed, the mites and associated faecal matter are vacuumed up under conditions whereby the vacuumed material does not vent into the surrounding atmosphere.

Spraying a mite-infested area with a composition according to this invention will effectively kill the mites which produce the allergens but, in order to provide rapid and effective control of dust mite allergens, the material comprising dead mites and associated faecal matter should be vacuumed up under conditions whereby this material is not vented into the ambient atmosphere. A central vacuum system, where the holding bag is remote from the area being cleaned, will fulfill this purpose. However, since this is not practical in most household operations, the alternative is to use a vacuum which has a high performance filter system, such as HEPA filters or a two-ply bag.

Although the compositions of this invention are effective in killing dust mites, in its broader aspect these compositions are an essential feature in a system for controlling the spread of mite-produced allergens. The invention therefore relates also to methods for controlling dust mite allergens in which the first essential step is killing the mites. As used herein, the term "control" refers to a process which involves killing the mites and then performing follow-up steps which involve removal of dead mites and their associated faecal matter.

The invention will be better understood by reference to the following examples, which are included for purposes of illustration only.

EXAMPLE 1

A quaternary ammonium-based concentration was prepared which had the following ingredients in the percentage indicated:

| Ingredient | % |
| --- | --- |
| Anhydrous ethanol[1] | 82.741 |
| Alkyl dimethylbenzyl ammonium quaternary salt | 0.334 |
| Benzyl benzoate[2] | 4.792 |
| Corrosion inhibitors | 0.500 |
| DI Water | 11.633 |
| | 100.000% |

The quaternary salt was added, under agitation, to a clean dry mixing vessel containing the anhydrous ethanol. Then, the benzyl benzoate was added, under agitation. When both of these ingredients had been dissolved, the remaining ingredients were then added.

An aerosol formulation was then prepared which contained 96% by weight of the above-described concentrate and 4% of carbon dioxide.

The pH range of the composition was from 9.0 to 10.6. The pressure range was from 95 to 105 p.s.i.g.

EXAMPLE 2

A formulation was prepared which used only ethanol as the antimicrobial agent. The formulation had the following constituents:

| Ingredient | % |
| --- | --- |
| Anhydrous Ethanol[1] | 79.167 |
| Dow Corning Surfactant 193[3] | 0.035 |
| Corrosion Inhibitors | 0.278 |
| Benzyl Benzoate | 6.390 |
| DI Water | 14.130 |

An aerosol spray formulation was made which contained 72% by weight of the above-described composition and 28% of H/C Butane 40.

EXAMPLE 3

Aerosol spray formulations were prepared containing the same ingredients following the process described in Example 1. The amounts of benzyl benzoate varied, but the percentage of other ingredients remain constant. The percentages of water were adjusted accordingly.

Each of the tested formulations was sprayed onto the surface of a mattress having an area of 3.09 square meters (queen size) in the amounts shown. Immediately thereafter, 25 live mites were placed on each mattress. The numbers of live and dead mites were counted after 24 hours and after 48 hours and the percentage kill rate was recorded. The following table shows the data for the initial results:

TABLE I

| | Benzyl Benzoate | Amount of Formulation | INITIAL RESULTS % of Dead Mites | |
| --- | --- | --- | --- | --- |
| Test No. | % | Sprayed | 24 Hours | 48 Hours |
| 1 | 0.163 | 85 g | 35.7 | 57.7 |
| 2 | 0.5 | 85 g | 32.0 | 56.8 |
| 3 | 1.0 | 57 g | 17.2 | 33.5 |
| 4 | 1.0 | 85 g | 51.0 | 70.6 |
| 5 | 4.6 | 57 g | 76.9 | 88.6 |
| 6 | 4.6 | 85 g | 96.1 | 99.2 |

Further tests were run on the mattress treated in Test No. 6. One week after the application of the product, and without application of any additional product, 25 live mites were placed on the mattress and the numbers of live mites and dead mites were observed after 24 hours and 48 hours. This procedure was repeated two weeks after application of product and three weeks after application of product, but again without the application of additional product. The kill percentages are shown in the following table:

TABLE II

| | RESULTS AFTER 1 WEEK % of Dead Mites | | RESULTS AFTER 2 WEEKS % of Dead Mites | | RESULTS AFTER 3 WEEKS % of Dead Mites | |
| --- | --- | --- | --- | --- | --- | --- |
| Test No. | 24 hrs | 48 hrs | 24 hrs | 48 hrs | 24 hrs | 48 hrs |
| 6 | 72.3 | 92.4 | 80.2 | 96.2 | 81.9 | 98.3 |

The foregoing data show the effectiveness of these formulations in killing dust mites and it should be particularly noted that formulation No. 6 has initially excellent results and shows a high level of residual effectiveness for as long as three weeks after application.

The invention has been described in detail with particular reference to preferred embodiments thereof, but it will be understood that variations and modifications can be effected within the spirit and scope of the invention as defined in the following claims.

We claim:

1. An aerosol composition for disinfection and for use in controlling dust mites which consists essentially of an effective amount of ethanol ranging from 50–85% and an acaricidally effective amount of benzyl benzoate ranging from 0.1–10%.

2. An aerosol composition according to claim 1 in which the benzyl benzoate is present in an amount of from 0.1% to 10.0% by weight, excluding propellant.

3. An aerosol composition according to claim 2 in which the benzyl benzoate is present in an amount of from 3.0% to 7.0% excluding propellant.

4. An aerosol composition for disinfection and for use in controlling dust mites which consists essentially of effective amounts of ethanol and one or more antimicrobial quaternary ammonium salts and an acaricidally effective amount of benzyl benzoate.

5. An aerosol composition for disinfection and for use in controlling dust mites which consists essentially of effective amounts of ethanol ranging from 50–85% and one or more antimicrobial phenolic compounds and an acaricidally effective amount of benzyl benzoate ranging from 0.1–10%.

6. A method for simultaneously sanitizing a textile surface and killing dust mites present thereon which comprises contacting said surface with an acaricidally effective amount of a composition consisting essentially of benzyl benzoate and ethanol.

7. A method according to claim 6 in which the composition is an aerosol composition.

8. A method according to claim 7 in which the composition consists essentially of one or more antimicrobial quaternary ammonium salts or one or more antimicrobial phenolic compounds, 0.1–10% benzyl, benzoate and 50–85% ethanol.

9. A method according to claim 8 in which the composition, excluding propellant, comprises from 0.1% to 10.0% by weight of benzyl benzoate.

10. A method for controlling allergens produced by dust mites which comprises the steps of (a) contacting a textile surface infested with said mites with an acaricidally effective amount of a composition consisting essentially of 0.1–10% benzyl benzoate and 50–85% ethanol;

(b) allowing a sufficient amount of time for the composition to dry and the mites to be killed; and (c) removing the dead mites and allergen-containing particles excreted by said mites.

11. A method according to claim 10 in which the composition is an aerosol composition.

12. A method according to claim 11 in which the removal of said dead mites and said particles is by means of a vacuum system which does not permit the removed material to vent into the ambient atmosphere.

13. A method according to claim 12 in which the composition consists essentially of one or more quaternary ammonium salts, 0.1–10% benzyl benzoate and 50–85% ethanol.

14. A method according to claim 13 in which, in the composition, the benzyl benzoate is present in an amount of from 0.1% to 10.0% by weight, excluding any propellant.

15. A method according to claim 14 in which, in the composition, the benzyl benzoate is present in an amount of from 3.0% to 7.0% by weight, excluding any propellant.

16. A method according to claim 12 in which the composition consists essentially of one or more antimicrobial phenolic compounds 0.1–10% , benzyl benzoate and 50–85% ethanol.

17. A method according to claim 16 in which, in the composition, the benzyl benzoate is present in an amount of from 0.1% to 10.0% by weight, excluding any propellant.

18. A method according to claim 17 in which, in the composition, the benzyl benzoate is present in an amount of from 3.0% to 7.0% by weight, excluding any propellant.

* * * * *

UNITED STATES PATENT AND TRADEMARK OFFICE
CERTIFICATE OF CORRECTION

PATENT NO. : 5,916,917
DATED : 29 June 1999
INVENTOR(S) : Janette SUH; Laura VACCARO; Robert BOGART and Dennis SMIALOWICZ It is certified that error appears in the above-identified patent and that said Letters Patent is hereby corrected as shown below:

On the title page, before "OTHER PUBLICATIONS" delete the reference "WO89/12673...3/48".

At column 11, line 41, delete the comma after "benzyl".

At column 12, line 33, insert a comma after the word "compounds" and delete the common after "0.1-10%".

Signed and Sealed this

Twenty-fifth Day of January, 2000

Attest:

Attesting Officer

Acting Commissioner of Patents and Trademarks

UNITED STATES PATENT AND TRADEMARK OFFICE
CERTIFICATE OF CORRECTION

PATENT NO.    : 5,916,917
DATED         : JUNE 29, 1999
INVENTOR(S)   : JANETTE SUH; LAURA VACARRO; ROBERT BOGART AND DENNIS SMIALOWICZ

It is certified that error appears in the above-identified patent and that said Letters Patent is hereby corrected as shown below:

On the title page, insert the following:

--[30] Foreign Application Priority Data

Feb. 20, 1997 [GB] United Kingdom....................9703531.50--

Signed and Sealed this

Twenty-ninth Day of August, 2000

Attest:

Attesting Officer

Q. TODD DICKINSON
Director of Patents and Trademarks